United States Patent [19]

Saito et al.

[11] Patent Number: 5,750,164
[45] Date of Patent: May 12, 1998

US005750164A

[54] METHOD OF DECREASING CHOLESTEROL CONCENTRATION IN FOOD

[75] Inventors: Chiaki Saito, Machida; Kozo Ohuchi, Hasuda, both of Japan

[73] Assignee: Kyowa Hakko Kogyo Co., Ltd., Tokyo, Japan

[21] Appl. No.: 709,327

[22] Filed: Sep. 5, 1996

Related U.S. Application Data

[63] Continuation of Ser. No. 538,048, Oct. 2, 1995, abandoned, which is a continuation of Ser. No. 368,761, Jan. 4, 1995, abandoned, which is a continuation of Ser. No. 103,040, Jul. 28, 1993, abandoned, which is a continuation of Ser. No. 810,340, Dec. 19, 1991, abandoned.

[30] Foreign Application Priority Data

Dec. 21, 1990 [JP] Japan ................... 2-405028

[51] Int. Cl.$^6$ ................... A23L 1/015; A23L 1/32
[52] U.S. Cl. ................... 426/47; 426/330; 426/614
[58] Field of Search ................... 426/47.33, 330.1, 426/605, 614

[56] References Cited

U.S. PATENT DOCUMENTS

| | | |
|---|---|---|
| 3,260,606 | 7/1966 | Azuma ................... 426/47 |
| 4,921,710 | 5/1990 | Beitz ................... 426/56 |

FOREIGN PATENT DOCUMENTS 0398666  11/1990  European Pat. Off. ................... 426/47

OTHER PUBLICATIONS

Aihara et al., Lebensmitttel–Wissenschaft und–Technologie, (1988) 21(6) 342–345, Abstract Only.

*Primary Examiner*—Anthony J. Weier
*Attorney, Agent, or Firm*—Antonelli, Terry, Stout, & Kraus, LLP

[57] ABSTRACT

Shown is a method of decreasing cholesterol concentration in eggs or processed egg foodstuffs, which includes hydrolyzing phospholipids in the eggs or processed egg foodstuffs with one member selected from the group of phospholipase $A_1$, $A_2$, B, D, lysophospholipase and a mixture thereof, and subjecting the phospholipid-hydrolyzed eggs or processed egg foodstuffs to a conventional cholesterol-decreasing treatment. Further, provided is a method of decreasing cholesterol concentration in meat, fish meat, dairy products, processed foodstuffs thereof, which includes hydrolyzing phospholipids in the meat, fish meat, dairy products, processed foodstuffs thereof with an enzyme having an activity of hydrolyzing the phospholipids in meat, fish meat, dairy products, processed foodstuffs thereof, and subjecting the phospholipid-hydrolyzed meat, fish meat, dairy products, processed foodstuffs thereof to a conventional cholesterol-decreasing treatment.

4 Claims, No Drawings

METHOD OF DECREASING CHOLESTEROL CONCENTRATION IN FOOD

This is a continuation application of Ser. No. 08/538,048, filed Oct. 2, 1995 now abandoned, which is a continuation of Ser. No. 08/368,761 (now abandoned), filed Jan. 4, 1995 which is a continuation application of Ser. No. 08/103,040, filed Jul. 28, 1993 (now abandoned), which is a continuation application of Ser. No. 07/810,340, filed Dec. 19, 1991, (now abandoned).

BACKGROUND OF THE INVENTION

The present invention relates to a method of decreasing cholesterol concentration in food and cholesterol-decreased food thus treated.

Cholesterol is highly contained in food such as egg, meat, fish meat, dairy products, etc. It is known that an excessive intake of cholesterol from these foodstuffs results in increasing serum cholesterol concentration, which causes coronary arterial heart disease [Dairy Council Digest, 60 (2) (1989)]. Accordingly, a need for cholesterol-decreased foodstuffs has been increasing in recent years, not only as diet for patients with hypercholesterolemia but also as daily food.

It is known that cholesterol-decreased food may be obtained by the physical and chemical methods, for example, by extracting cholesterol from food with hexane or acetone (Japanese Published Examined Patent Application No. 42944/71 and Japanese Published Unexamined Patent Application No. 19062/72) and by supercritical carbon dioxide extraction (Japanese Published Unexamined Patent Application Nos. 135847/84 and 167035/90).

It is also known that cholesterol-decreased butter may be obtained by adsorbing cholesterol using polymer-supported digitonin having a high affinity to cholesterol [J. Agric. Food. Chem., 38 (9), 1839 (1990)].

It is also known that cholesterol-decreased food may be obtained by putting the egg yolk solution or milk products into contact with β-cyclodextrin having a high affinity to cholesterol, and then separating insoluble complex of the cholesterol and the β-cyclodextrin by centrifugation (Japanese Published Unexamined Patent Application Nos. 252259/89, 98553/91 and 49647/91).

On the other hand, as biochemical methods, a method of degrading cholesterol in food with microorganism [Japanese Published Unexamined Patent Application No. 267231/88, J. of Food Science, 53 (2), 659 (1989)] and a method of converting cholesterol with cholesterol reductase to coprostanol, non-absorbable sterol [FASEB Journal, 2 (4), 1660 (1988)] are known.

The enzymatic conversion with cholesterol reductase is a method of converting cholesterol to coprostanol without deteriorating the quality of food (USP 4,921,710).

In the physical and chemical methods described above, there is a problem that fats, proteins, pigments and flavor components are also extracted, in addition to cholesterol, to cause deterioration of the quality. For this reason, it has been desired to develop a method of selectively decreasing cholesterol concentration in food.

On the other hand, the biochemical methods including the enzymatic method are excellent in causing no deterioration of the food quality. However, since food cholesterol exists in lipoprotein, biomembrane, or fatty granule [Biochim. Biophys. Acta, 164, 566 (1968)], the biochemical methods including enzymatic methods are hardly applicable.

It is further reported that in the case of using water-soluble enzyme, the enzyme hardly acts on cholesterol in fat portions and hence it is effective to combine supercritical fluid methods with enzymatic conversion [Spectrum Food Industry, 6 (2), 21 (1989)].

It is reported that in the degradation of cholesterol in egg yolk by extracellular enzymes of *Rhodococcus equi* No. 23, the simultaneous action of phospholipase C accelerates the reaction [Lebensmittel-Wissenshaft und-Technologie) 21, (6) 342 (1988)].

However, it is impossible to degrade cholesterol in egg yolk perfectly by simultaneous action of phospholipase C, and such treated egg yolk has the lowering functional properties. So, it is not good for the industrial uses.

It has thus been desired to develop and effective biochemical method of decreasing cholesterol in food.

SUMMARY OF THE INVENTION

According to the present invention, there is provided a method of decreasing cholesterol concentration in eggs or processed egg foodstuffs, which comprises hydrolyzing phospholipids in the eggs or processed egg foodstuffs with one member selected from the group consisting of phospholipase $A_1$, $A_2$, B, D, lysophospholipase and a mixture thereof, and subjecting the phospholipid-hydrolyzed eggs or processed egg foodstuffs to a conventional cholesterol-decreasing treatment. Further, provided is a method of decreasing cholesterol concentration in meat, fish meat, dairy products, processed foodstuffs thereof, which comprises hydrolyzing phospholipids in meat, fish meat, dairy products, processed foodstuffs thereof with an enzyme having an activity of hydrolyzing the phospholipids and subjecting the phospholipid-hydrolyzed meat, fish meat, dairy products, processed foodstuffs thereof to a conventional cholesterol-decreasing treatment.

DESCRIPTION OF THE INVENTION

The term "foodstuff" appearing hereinafter means eggs or processed egg foodstuffs, meat or processed meat foodstuffs, fish meat or processed fish meat foodstuffs, and dairy products or processed dairy foodstuffs. The present invention is similarly applicable to these foodstuffs.

The term "to hydrolyze phospholipids" as used herein means to hydrolyze the ester bond of phospholipids.

As the enzyme to be used in hydrolyzing phospholipids, mention may be made of phospholipase $A_1$ (EC 3.1.1.32) phospholipase $A_2$, (EC 3.1.1.4), phospholipase B (EC 3.1.1.5), phospholipase C (EC 3.1.4.3), phospholipase D (EC 3.1.4.4), lysophospholipase (EC 3.1.1.5), etc. The enzymes are used alone or in combination. Further, any of an animal tissue, a plant tissue and a microbial cell, producing the enzyme may be used so long as it is capable of hydrolyzing phospholipids. A culture of the animal tissue, the plant tissue or the microbial cell, and a treated product of the culture may be used as well.

Specifically, phospholipase $A_1$, $A_2$, B or D is preferred for decreasing cholesterol concentration in eggs and processed egg foodstuffs, and phospholipase B, C or D is preferred for decreasing cholesterol concentration in meat, fish meat, dairy products, processed foodstuffs thereof.

Phospholipase $A_1$ and phospholipase $A_2$ are enzymes which hydrolyze phospholipid into free fatty acid and monoacyl-type phospholipid and are derived from animals (swine or bovine pancreas) or microorganisms [Protein, Nucleic Acid, Enzyme, 31 (15), 1661 (1986)].

Phospholipase B is an enzyme which hydrolyzes phospholipid into free fatty acid and glycerophosphate base (choline glycerophosphate, ethanolamine glycerophosphate) and is derived from animals or microorganisms [Protein, Nucleic Acid, Enzyme, 31 (3), 247 (1986)].

Phospholipase C is an enzyme which hydrolyzes phospholipid into diacyl glyceride and phosphate base (choline phosphate or ethanolamine phosphate) and is derived from microorganisms [Protein, Nucleic Acid, Enzyme, 31 (5), 455 (1986)].

Phospholipase D is an enzyme which hydrolyzes phospholipid into phosphatidic acid and base (choline or ethanolamine) and is derived from microorganisms or plants [Protein, Nucleic Acid, Enzyme, 31 (6), 553 (1986), Japanese Published Unexamined Patent Application Nos. 99386/73, 44049/79, 63388/83, 152481/83, 219373/88 and 222679/90].

Lysophospholipase is an enzyme which hydrolyzes monoacyl phospholipid into free fatty acid and glycerophosphate base.

The enzymes described above are commercially available and readily accessible. There are, for example, Lecitase (derived from swine pancreas: phospholipase $A_2$, manufactured by NOVO Co.), Phospholipase $A_2$ (P8913) (derived from swine pancreas: manufactured by Sigma Inc.), Phospholipase B (P8914) (derived from the genus Vibrio, manufactured by Sigma Inc.), Phospholipase C (P6135) (derived from the genus Bacillus, manufactured by Sigma Inc.), Phospholipase C (P7633) (derived from the genus Chlostridium, manufactured by Sigma Inc.), Phospholipase D (P8023) (derived from the genus Streptomyces, manufactured by Sigma Inc.), Phospholipase D (P4912) (derived from the genus Streptomyces, manufactured by Sigma Inc.), Phospholipase D (P7758) (derived from cabbage, manufactured by Sigma Inc.), etc.

The enzymes such as phospholipase $A_1$, $A_2$, B, C, D and lysophospholipase, etc. may be added to or mixed with a foodstuff as they are or in the form of their aqueous solution. Alternatively, the enzyme is immobilized to a carrier and a foodstuff is brought into contact with the carrier. The reaction is carried out at a temperature of 2° to 70° C., preferably 5° to 50° C. for 10 seconds to 100 hours, preferably 60 seconds to 50 hours, whereby the ester bond of phospholipids in the foodstuffs is hydrolyzed. An amount of the enzyme is $1 \times 10^{-1}$ to $1 \times 10^5$, preferably 1 to $1 \times 10^4$ units per gram by weight of phospholipids in the foodstuffs.

During the treatment with the phospholipase, the pH of the foodstuffs may be set to fit the pH originally possessed by foodstuffs or fit the pH of processed foodstuffs.

As the cholesterol-decreasing treatment which is performed in the method of the present invention, not only the already known treatments for decreasing cholesterol but also any other cholesterol-decreasing treatments which are being developed, may be used. Examples of the treatment include, as biochemical methods, a treatment by the enzyme system which oxidize, reduce or degrade cholesterol (e.g., cholesterol oxidase, cholesterol reductase), a treatment by the microorganism which catalyzes the same reaction (e.g., genus Eubacterium, genus Nocardia, genus Lactobacillus), and the like. As the physical and chemical methods, there are treatments by extraction of cholesterol with an organic solvent such as acetone, hexane, etc. or with supercritical carbon dioxide and so on. Furthermore, there are methods by adsorption using β-cyclodextrin, digitonin immobilized on a carrier, activated carbon, etc.

The hydrolyzation of phospholipids is carried out in or before the cholesterol-decreasing treatment. If the cholesterol-decreasing treatment inhibits hydrolyzation of phospholipids, it should be carried out after hydrolyzing the phospholipids with the enzyme described above. This method of the present invention accelerates decrease of cholesterol content and selectively decreases cholesterol concentration.

Hereafter the present invention is described with examples and reference examples.

EXAMPLE 1

In 30 ml of an enzyme solution containing cholesterol oxidase (CHOD) and phospholipase D (PL-D) (manufactured by Sigma Inc.) or phospholipase C (PL-C) (manufactured by Sigma Inc.) having the activity units shown in Table 1, 10 g of ham block was immersed at 5° C. for 24 hours to give the enzyme-treated ham block. A sample which was immersed in water containing no enzyme was made as control group. The activity of the enzyme used was determined by the following method.

The cholesterol oxidase activity was determined by the method of Uwajima et al. [Agricultural and biological Chemistry, 42 (7), 1453 (1978)]. The phospholipase D activity was determined by the following method. After 0.5 ml of 50 mM Tris hydrochloride buffer (pH 7.0) was mixed with 0.5 ml of 6% purified soya lecithin emulsion (0.6 g of purified soya lecithin, 10 ml of distilled water), 0.01 ml of enzyme solution was added to the mixture. After reaction at 37° C. for 10 minutes, 0.5 ml of 15% trichloroacetic acid aqueous solution was added to terminate the reaction. Next, choline produced in the reaction solution was measured by Determiner ChE (manufactured by Kyowa Medex Co.). The same procedure was repeated using the reaction solution containing the enzyme which had been inactivated by heating. An enzyme activity which releases 1 μmol of choline for one minute is defined as one unit. The activity of phospholipase C was determined according to the method of Taguchi et al. [Biochimica et Biophysica Acta, 409, 75 (1975)].

The rate of decreased cholesterol of the resulting ham block was determined by the following method. First, the treated ham block was freeze-dried and then ground into powder. The lipid fraction was extracted from the powder with a mixture of chloroform and methanol (2:1). Cholesterol (CHOL) and 4-cholestenone (4-ONO) formed by the enzymatic conversion in lipid fractions were measured by gas chromatography (Gasukuro Kogyo, OV-17, column temperature of 270° C. The rate of decreased cholesterol is shown by mol %=[4-ONO/(CHOL+4-ONO)]×100. The results are shown in Table 2.

TABLE 1

| Treated Group | Enzyme concentration (unit/ml) | | |
|---|---|---|---|
| | CHOD | PL-C | PL-D |
| 1 (control) | — | — | — |
| 2 | 50 | — | — |
| 3 | 50 | 15 | — |
| 4 | 50 | — | 40 |

TABLE 2

| Treated Group | Rate of decreased cholesterol (mol %) |
|---|---|
| 1 (control) | 0.0 |
| 2 | trace |

TABLE 2-continued

| Treated Group | Rate of decreased cholesterol (mol %) |
|---|---|
| 3 | 50.1 |
| 4 | 65.2 |

The foregoing results reveal that the cholesterol-decreased meat was obtained.

EXAMPLE 2

Cholesterol oxidase and phospholipase D or phospholipase C having the activity units shown in Table 3 were blended with 10 g of minced meat. The blend was kept at 5° C. for 24 hours to give the treated minced meat. A sample to which no enzyme was added was made as control group.

The treated minced meat was freeze-dried to give a sample. The rate of decreased cholesterol in the meat was determined according to the method of Example 1. The results are shown in Table 4.

TABLE 3

| | Amount of Enzyme Added (unit/g Meat) | | |
|---|---|---|---|
| Treated Group | CHOD | PL-C | PL-D |
| 1 (control) | — | — | — |
| 2 | 20 | — | — |
| 3 | 20 | 1.5 | — |
| 4 | 20 | 30 | — |
| 5 | 20 | — | 0.8 |
| 6 | 20 | — | 16 |
| 7 | 2 | — | — |
| 8 | 10 | — | — |
| 9 | 40 | — | — |
| 10 | 2 | — | 8 |
| 11 | 10 | — | 8 |
| 12 | 40 | — | 8 |

TABLE 4

| Treated Group | Rate of decreased cholesterol (mol %) |
|---|---|
| 1 (control) | 0.0 |
| 2 | trace |
| 3 | 86.8 |
| 4 | 93.7 |
| 5 | 57.5 |
| 6 | 98.2 |
| 7 | trace |
| 8 | trace |
| 9 | trace |
| 10 | 76.9 |
| 11 | 78.3 |
| 12 | 88.2 |

The foregoing results reveal that the cholesterol-decreased meat was obtained.

EXAMPLE 3

After cholesterol oxidase and standard phospholipase B preparation obtained in Reference Example 1 having the activity units shown in Table 5 were blended with 10 g of minced meat. The blend was kept at 5° C. for 48 hours to give the treated minced meat. A sample to which no enzyme was added was made as control group.

The treated minced meat was freeze-dried to give a sample. The rate of decreased cholesterol in the meat was determined according to the method of Example 1. The results are shown in Table 6.

TABLE 5

| | Amount of Enzyme Added (unit/g Meat) | |
|---|---|---|
| Treated Group | CHOD | PL-B |
| 1 (control) | — | — |
| 2 | 10 | — |
| 3 | 10 | 0.25 |
| 4 | 10 | 0.5 |
| 5 | 10 | 1.0 |
| 6 | 10 | 2.5 |

TABLE 6

| Treated Group | Rate of decreased cholesterol (mol %) |
|---|---|
| 1 (control) | 0.0 |
| 2 | trace |
| 3 | 2.5 |
| 4 | 6.5 |
| 5 | 14.4 |
| 6 | 24.5 |

The foregoing results reveal that the cholesterol-decreased meat was obtained.

EXAMPLE 4

Cholesterol oxidase and phospholipase D or phospholipase C having the activity units shown in Table 7 were blended with log each of minced ham. minced chicken white meat and minced round of beef and sardine paste. Each blend was kept at 5° C. for 24 hours to give the treated minced meat and paste. A sample to which no enzyme was added was made as control group. The treated meat and paste were freeze-dried to give samples. The rate of decreased cholesterol was determined according to the method of Example 1. The results are shown in Table 8.

TABLE 7

| | Amount of Enzyme Added (unit/g Meat) | | |
|---|---|---|---|
| Treated Group | CHOD | PL-C | PL-D |
| 1 (control) | — | — | — |
| 2 | 8 | — | — |
| 3 | 8 | 8 | — |
| 4 | 8 | — | 8 |

TABLE 8

| Treated Group | Rate of decreased cholesterol (mol %) |
|---|---|
| (ham) | |
| 1 (control) | 0.0 |
| 2 | trace |
| 3 | 65.0 |
| 4 | 76.2 |
| (chicken white meat) | |
| 1 (control) | 0.0 |
| 2 | trace |
| 3 | 76.0 |
| 4 | 88.7 |

TABLE 8-continued

| Treated Group | Rate of decreased cholesterol (mol %) |
|---|---|
| (round of beef) | |
| 1 (control) | 0.0 |
| 2 | trace |
| 3 | 80.2 |
| 4 | 83.4 |
| (sardine) | |
| 1 (control) | 0.0 |
| 2 | trace |
| 3 | 40.3 |
| 4 | 66.7 |

The foregoing results reveal that the ham, round of beef, chicken white meat and sardine having decreased cholesterol content were obtained.

EXAMPLE 5

Cholesterol oxidase and phospholipase $A_2$ (PL-$A_2$) (lecitase, manufactured by NOVO Co., 10000 units/ml), phospholipase D or phospholipase C having the activity units shown in Table 9 were added to 50 g of egg yolk. The egg yolk was treated at 37° C. for 3 hours to give the treated egg yolk. A sample to which no enzyme was added was made as control group. The activity of phospholipase $A_2$ was determined by the following method.

0.4 ml of 50 mM Tris hydrochloride buffer (pH 7.0) and 0.1 ml of 100 mM calcium chloride solution were mixed with 0.5 ml of 2% purified soya lecithin emulsion (0.2 g of purified soya lecithin, 10 ml of distilled water), and 0.01 ml of enzyme solution was added to the mixture. After reaction at 37° C. for 10 minutes, 0.5 ml of 15% trichloroacetic acid aqueous solution was added to terminate the reaction. Next, the free fatty acid produced in the reaction solution was then measured by Determiner NEFA (manufactured by Kyowa Medex Co.). The same procedure was repeated using the reaction solution containing the enzyme inactivated by heating. An enzyme activity which releases 1 μmol of fatty acid for one minute is defined as one unit.

The treated egg yolk was freeze-dried and the lipid fraction was extracted from the obtained sample with ethyl acetate followed by fractionation. The conversion rate of decreasing cholesterol was determined according to the method of Example 1. The results are shown in Table 10, where the similarly treated egg yolk except that phospholipase C was used instead of phospholipase $A_2$ or D, was made as comparison group.

TABLE 9

| Treated Group | Amount of Enzyme Added (unit/g Egg Yolk) | | | |
|---|---|---|---|---|
| | CHOD | PL-C | PL-$A_2$ | PL-D |
| 1 (control) | — | — | — | — |
| 2 | 400 | — | — | — |
| 3 | 400 | — | 10 | — |
| 4 | 400 | — | 200 | — |
| 5 | 400 | — | — | 4 |
| 6 | 400 | — | — | 80 |
| 7 | 40 | — | — | — |
| 8 | 200 | — | — | — |
| 9 | 800 | — | — | — |
| 10 | 40 | — | — | 40 |
| 11 | 200 | — | — | 40 |
| 12 | 800 | — | — | 40 |

TABLE 9-continued

| Treated Group | Amount of Enzyme Added (unit/g Egg Yolk) | | | |
|---|---|---|---|---|
| | CHOD | PL-C | PL-$A_2$ | PL-D |
| Comparison group | 400 | 8 | — | — |
| | 400 | 160 | — | — |

TABLE 10

| Treated Group | Rate of decreased cholesterol (mol %) |
|---|---|
| 1 (control) | 0.0 |
| 2 | 34.0 |
| 3 | 54.1 |
| 4 | 78.6 |
| 5 | 77.7 |
| 6 | 96.1 |
| 7 | 10.5 |
| 8 | 26.3 |
| 9 | 48.5 |
| 10 | 83.4 |
| 11 | 97.0 |
| 12 | 99.1 |
| Comparison group | 50.3 |
| | 58.8 |

The foregoing results reveal the rate of decreasing cholesterol by treating with phospholipase D is higher than that of phospholipase C.

EXAMPLE 6

3 g of table salt, 0.5 g of Polygon C (manufactured by Chiyoda Chemical Industry Co., Ltd.) and 2.5 mg of nitrite were blended with 100 g of minced ham. Cholesterol oxidase and phospholipase D or phospholipase C having the activity units shown in Table 11 were blended with the mixture. The mixture was stuffed into a casing. After keeping at 5° C. for 12 hours, the casing was heated at 70° C. for 15 minutes to give a sausage. A sample to which no enzyme was added was made as control group.

The cooked sausage was freeze-dried to give a powdery sample. The rate of decreased cholesterol was determined according to the method of Example 1. The results are shown in Table 12.

TABLE 11

| Treated Group | Amount of Enzyme Added (unit/g Meat) | | |
|---|---|---|---|
| | CHOD | PL-C | PL-D |
| 1 (control) | — | — | — |
| 2 | 10 | — | — |
| 3 | 10 | 4 | — |
| 4 | 10 | — | 4 |

TABLE 12

| Treated Group | Rate of decreased cholesterol (mol %) |
|---|---|
| 1 (control) | 0.0 |
| 2 | 1.3 |
| 3 | 58.7 |
| 4 | 66.2 |

The foregoing results reveal that the sausage having decreased cholesterol content was obtained.

EXAMPLE 7

Phospholipase D having the activity unit shown in Table 13 was added to 50 g of egg yolk. The mixture was treated at 37° C. for 3 hours to give the treated egg yolk. A sample to which no enzyme was added was made as control group. The treated egg yolk was freeze-dried to give a powdery sample. To 10 g each of the powdery sample was added 100 ml of cold acetone (5° C.). After stirring for a minute, the sample was centrifuged to give cholesterol-extracted dry egg yolk powders. The extraction efficiency and selectivity of cholesterol were determined by the cholesterol content and triglyceride content in acetone used for the extraction. The cholesterol content was measured by gas chromatography, and triglyceride was measured by TLC/FID IATROSCAN (manufactured by Diatron Co.)

The cholesterol extraction amount in each sample is shown by relative value (%) when the cholesterol extraction amount in the control group is made 100%. The triglyceride extraction amount in each sample is shown by relative value (%) when the triglyceride extraction amount in the control group is made 100%. The results are shown in Table 14.

TABLE 13

| Treated Group | Amount of PL-D Added (unit/g Egg Yolk) |
| --- | --- |
| 1 (control) | — |
| 2 | 0.06 |
| 3 | 0.6 |
| 4 | 6 |
| 5 | 30 |

TABLE 14

| Treated Group | Amount of Cholesterol Extracted (%) | Amount of Triglyceride Extracted (%) |
| --- | --- | --- |
| 1 (control) | 100 | 100 |
| 2 | 110 | 92 |
| 3 | 112 | 96 |
| 4 | 114 | 88 |
| 5 | 121 | 97 |

The foregoing results reveal that the egg yolk having selectively decreased cholesterol content was obtained.

EXAMPLE 8

20% egg yolk aqueous solution was centrifuged at 10000×G for 15 minutes to obtain the supernatant. To 25 ml of the supernatant was added 30 units of phospholipase D. The mixture was treated at 37° C. for 3 hours to give the treated egg yolk. A sample to which no enzyme was added was made as control group. The egg yolk was passed through a column packed with a digitonin-immobilized polymer which was prepared by the method of Reference Example 2 (bed volume: 30 ml). Furthermore 40 ml of water was passed through the column to recover the egg yolk aqueous solution. The treated egg yolk aqueous solution thus obtained was freeze-dried to give powdery samples. A solvent for extraction (chloroform:methanol:acetic acid= 2:1:0.1) was added to these powdery samples. After stirring for 30 minutes, the mixture was centrifuged to give the extract of the lipid fraction as the supernatant.

The rate of cholesterol adsorbed and the rate of triglyceride adsorbed in the treated egg yolk solution were determined by analyzing the extract of the lipid fraction described above by the method described in Example 7. The results are shown in Table 15.

TABLE 15

| Treated Group | Amount of Cholesterol Adsorbed (%) | Amount of Triglyceride Adsorbed (%) |
| --- | --- | --- |
| Control group | 30 | 28 |
| PL-D-treated group | 33 | 14 |

The foregoing results reveal that the egg yolk solution having selectively decreased cholesterol content was obtained.

EXAMPLE 9

After 3.4 g of table salt, 30 mg of spice and 2.5 mg of nitrite were blended with 100 g of minced ham. phospholipase D or phospholipase C having the activity units shown in Table 16 were added to the blend. Furthermore, the cells prepared by the method of Reference Example 3 were added thereto and mixed with each other. The mixture was stuffed into a casing. The casing was kept at 30° C. under 90% RH for 15 hours to undergo fermentation. Thereafter the casing was dried at a temperature of 30° C. under 50% RH for 9 hours to give a dry sausage. A sample to which no enzyme was added was made as control group. The cooked sausage was freeze-dried to give a sample. The rate of decreased cholesterol in the sample was determined according to the method of Example 1. The results are shown in Table 17.

TABLE 16

| | Amount of Cell Added (unit/g Meat) | | |
| --- | --- | --- | --- |
| Treated Group | Cell (dry weight g) | PL-C | PL-D |
| 1 (control) | — | — | — |
| 2 | 0.03 | — | — |
| 3 | 0.03 | 4 | — |
| 4 | 0.03 | — | 4 |

TABLE 17

| Treated Group | Rate of decreased cholesterol (mol %) |
| --- | --- |
| 1 (control) | 0.0 |
| 2 | 12.8 |
| 3 | 35.3 |
| 4 | 38.8 |

The foregoing results reveal that the fermented dry sausage having decreased cholesterol content was obtained.

EXAMPLE 10

After cholesterol oxidase and phospholipase B, phospholipase D or phospholipase C having the activity units shown in Table 18 were added to and mixed with 100 g of egg yolk. The mixture was treated at 37° C. for 3 hours to give an enzyme-treated egg yolk. A scramble egg was prepared by adding 20 ml of milk to the treated egg, melting 20 g of butter on a pan, putting the egg solution and continuously scrambling the mixture on the soft fire. A sample to which no enzyme was added was made as control group.

The cooked scrambled egg was freeze-dried. The lipid fraction was extracted and fractionated from the obtained sample with a solvent (chloroform:methanol:acetic acid= 2:1:0.1). The rate of decreased cholesterol in the obtained sample was determined according to the method of Example 1. The results are shown in Table 19, where the similarly treated scrambled egg except that phospholipase C was used instead of phospholipase B or D, was made as comparison group.

TABLE 18

| Treated Group | Amount of Enzyme Added (unit/g Egg) | | | |
|---|---|---|---|---|
| | CHOD | PL-C | PL-B | PL-D |
| 1 (control) | — | — | — | — |
| 2 | 200 | — | — | — |
| 3 | 200 | — | 4 | — |
| 4 | 200 | — | 80 | — |
| 5 | 200 | — | — | 2 |
| 6 | 200 | — | — | 40 |
| Comparison group | 200 | 4 | — | — |
| | 200 | 80 | — | — |

TABLE 19

| Treated Group | Rate of decreased cholesterol (mol %) |
|---|---|
| 1 (control) | 0.0 |
| 2 | 29.4 |
| 3 | 80.1 |
| 4 | 96.6 |
| 5 | 81.2 |
| 6 | 98.5 |
| Comparison group | 51.1 |
| | 62.8 |

The foregoing results reveal that the rate of decreasing cholesterol by treating with phospholipase B or D is higher than that of phospholipase C.

EXAMPLE 11

After cholesterol oxidase and phospholipase D or phospholipase C having the activity units shown in Table 20 were added to and mixed with 100 ml of milk. The mixture was kept at 50° C. for 3 hours to give a treated milk. A sample to which no enzyme was added was made as control group.

The treated milk was freeze-dried. The rate of decreased cholesterol in the obtained sample was determined according to the method of Example 1. The results are shown in Table 21.

TABLE 20

| Treated Group | Amount of Enzyme Added (unit/g Milk) | | |
|---|---|---|---|
| | CHOD | PL-C | PL-D |
| 1 (control) | — | — | — |
| 2 | 5 | — | — |
| 3 | 5 | 4 | — |
| 4 | 5 | — | 2 |

TABLE 21

| Treated Group | Rate of decreased cholesterol (mol %) |
|---|---|
| 1 (control) | 0.0 |
| 2 | 33.1 |

TABLE 21-continued

| Treated Group | Rate of decreased cholesterol (mol %) |
|---|---|
| 3 | 72.3 |
| 4 | 66.9 |

The foregoing results reveal that the milk having decreased cholesterol content was obtained.

EXAMPLE 12

After 20% egg yolk aqueous solution was centrifuged at 10000×G for 15 minutes, a supernatant was obtained. The supernatant (50 ml) was passed through a column packed with the phospholipase D-immobilized polymer described in Reference Example 4 or a control polymer as described in Reference Example 4 (bed volume:20 ml) at a temperature of 50° C. at a flow rate of 0.5 ml/min. After 240 activity units of cholesterol oxidase was added to 30 ml of the elution, the mixture was treated at 37° C. for 3 hours to give a cholesterol-decreased egg yolk. The treated egg yolk was freeze-dried and a lipid fraction was extracted from the obtained sample with ethyl acetate and fractionated. The rate of decreased cholesterol in the obtained sample was determined by the method of Example 1. The results are shown in Table 22.

TABLE 22

| Treated Group | Rate of decreased cholesterol (mol %) |
|---|---|
| Control group | 11.3 |
| PL-D-treated group | 86.6 |

The foregoing results reveal that the egg yolk solution having decreased cholesterol content was obtained.

EXAMPLE 13

Phospholipase D having the activity units shown in Table 23 was added to 1 kg of 20% egg yolk solution. A sample to which no enzyme was added was made as control group. The mixture was incubated at 50° C. for 20 hours to give an enzyme-treated egg yolk, and then dried with MINI-SPRAY DRYER (manufactured by Yamato Science Co.). 10 g of the dried egg yolk was extracted with supercritical carbon dioxide at 163 atm/40° C. using supercritical fluid extraction apparatus (SUPER-200 by Nihon Bunko Co.). Flow was continued until 45 g carbon dioxide for each gram of the sample had been passed through the sample. The total lipid was extracted from control egg yolk and $CO_2$ extracted egg yolk with a mixture of chloroform and methanol (2:1). Then cholesterol and triglyceride in total lipid were measured by TLC/FID IATROSCAN.

The rate of remaining cholesterol and triglyceride is shown by mol %=(cholesterol or triglyceride from $CO_2$ extracted egg yolk)÷(cholesterol or triglyceride from $CO_2$-untreated egg yolk)×100, defining the amount of cholesterol or triglyceride in the sample untreated with the extraction with supercritical carbon dioxide as 100%. The results are shown in Table 24.

TABLE 23

| Treated Group | Amount of PL-D Added (unit/g Egg Yolk) |
|---|---|
| 1 (control) | 0 |
| 2 | 0.2 |

TABLE 24

| Treated Group | Remaining cholesterol (mol %) | Remaining triglyceride (mol %) |
|---|---|---|
| 1 (control) | 91 | 91 |
| 2 | 67 | 93 |

The foregoing results reveal that the excellent egg yolk having selectively decreased cholesterol content was obtained.

EXAMPLE 14

Phospholipase D having the activity units shown in Table 25 was added to 50 g of 15% egg yolk solution. A sample to which no enzyme was added was made as control group. The mixture was incubated at 50° C. for 20 hours to give the enzyme-treated egg yolk. The treated egg yolk was put into contact with 1.5 g of β-cyclodextrin under stirring for 5 minutes at 20° C., and the mixture was centrifuged at 8000×G for 20 minutes. A sample to which β-cyclodextrin was not added was made as control egg yolk. The total lipid was extracted from β-cyclodextrin-untreated egg yolk and β-cyclodextrin-treated egg yolk with a mixture of chloroform and methanol (2:1), and then cholesterol and triglyceride in the total lipid were measured by TLC/FID IATROSCAN.

The rate of remaining cholesterol and triglyceride is shown by mol %=(cholesterol or triglyceride from $CO_2$ extracted egg yolk÷cholesterol or triglyceride from β-cyclodextrin-untreated egg yolk)×100. The results are shown in Table 26.

TABLE 25

| Treated Group | Amount of PL-D Added (unit/g Egg Yolk) |
|---|---|
| 1 (control) | 0 |
| 2 | 2 |

TABLE 26

| Treated Group | Remaining cholesterol (mol %) | Remaining triglyceride (mol %) |
|---|---|---|
| 1 (control) | 5 | 36 |
| 2 | 0 | 102 |

The foregoing results reveal that the excellent egg yolk having selectively decreased cholesterol content was obtained.

EXAMPLE 15

Phospholipase D having the activity units shown in Table 27 was added to 500 ml of 20% egg yolk solution. A sample to which no enzyme was added was made as control group. The mixture was incubated at 50° C. for 20 hours to give the enzyme-treated egg yolk. The treated egg yolk was put into contact with 20 g of β-cyclodextrin. After this contact under stirring for 5 minutes at 20° C., the mixture was centrifuged at 8000×G for 30 minutes. The egg yolk solutions were freeze-dried. The weight of dried samples was measured. The results are shown in Table 28, where the weight of the dried samples treated with S-cyclodextrin is expressed, defining the weight of dried sample untreated with β-cyclodextrin as 100%.

The total cholesterol was extracted from β-cyclodextrin-untreated egg yolk and β-cyclodextrin-treated egg yolk with a mixture of chloroform and methanol (2:1), and then cholesterol was measured by TLC/FID IATROSCAN.

The rate of remaining cholesterol is shown by mol %=(cholesterol from treated egg yolk÷cholesterol from β-cyclodextrin-untreated egg yolk)×100, defining the total cholesterol in β-cyclodextrin-untreated egg yolk as 100%. The results are shown in Table 29.

TABLE 27

| Treated Group | Amount of PL-D Added (unit/g Egg Yolk) |
|---|---|
| 1 (control) | 0 |
| 2 | 0.2 |
| 3 | 1 |

TABLE 28

| Treated Group | Dried weight (%) |
|---|---|
| 1 (control) | 59 |
| 2 | 95 |
| 3 | 98 |

TABLE 29

| Treated Group | Remaining cholesterol (mol %) |
|---|---|
| 1 (control) | 7.7 |
| 2 | 1.4 |
| 3 | 0.7 |

The foregoing results reveal that the excellent egg yolk having selectively decreased cholesterol content was obtained.

Reference Example 1

Phospholipase B-producing bacterium (*Streptomyces scabies* ATCC 15485) was inoculated into a medium (2% soluble starch, 0.1% $KNO_3$, 0.05% $K_2HPO_4$, 0.05% magnesium sulfate heptahydrate, 0.05% sodium chloride, 1% calcium carbonate, 1% meat extract, 1% polypeptone, 0.5% soybean phospholipid), and cultured at 28° C. for 96 hours.

Protein in the culture supernatant was recovered by 80% ethanol fractionation. After this active fraction was adsorbed onto DEAE Sepharose CL-6B [10 mM Tris hydrochloride buffer (pH 8.0)], the fraction was eluted by increasing the ionic strength with 0.5M sodium chloride. Phospholipase B was collected in terms of the activity determined by the method described below.

The activity of phospholipase B was determined by the following method. After 0.5 ml of 50 mM Tris hydrochloride buffer (pH 7.0) was mixed with 0.5 ml of 2% purified soya lecithin emulsion (0.2 g of purified soya lecithin, 10 ml of distilled water), 0.01 ml of the enzyme solution was added to the mixture. After incubation at 37° C. for 10 minutes, 0.5 ml of 15% trichloroacetic acid aqueous solution was added to terminate the reaction. Next, the free fatty acid produced in the reaction solution was measured by Determiner NEFA (manufactured by Kyowa Medex Co.). The same procedure was repeated using the reaction solution containing the enzyme which had been inactivated by heating. An enzyme activity which releases 2 μmol of the fatty acid for one minute is defined as one unit.

Reference Example 2

Epoxy-activated Sepharose (manufactured by Pharmacia) was added to 50% dimethylformamide aqueous solution (pH 12.5) of 6.4 mM digitonin. The mixture was reacted for 48 hours at 45° C., and pH 12.5. After completion of the reaction, the prepared polymer was washed with 0.1M borate buffer (pH 8.0) and then with 0.1M acetate buffer (pH 4.0). Then, the polymer was allowed to stand overnight in 1.0M ethanolamine aqueous solution and further washed with water to give the digitonin-immobilized polymer.

Reference Example 3

Cholesterol oxidase-producing bacterium (*Brevibacterium sterolicum* ATCC 21387) was inoculated into 10 ml of bouillon medium, and cultured with shaking at 30° C., to prepare a seed culture.

10 ml of the seed culture was inoculated into 1 l of a medium (3% corn steep liquor, 2% polypeptone, 0.2% sodium nitrate, 0.1% monopotassium phosphate, 0.05% potassium chloride, 0.05% magnesium sulfate, pH 7.3) for producing cholesterol oxidase and cultured with shaking at 30° C. for 24 hours. After completion of the culturing, the culture was centrifuged at 10000×G for 20 minutes to give the cells.

Reference Example 4

10 g of the freeze-dried CNBr-activated Sepharose (manufactured by Pharmacia) was swollen and washed with 2 l of 1 mM hydrochloric acid aqueous solution. This polymer was added to a phospholipase D solution [solution of 700 mg of phospholipase D (manufactured by Sigma Inc.) in 0.1M NaHCO$_3$ buffer (pH 8) containing 0.5M NaCl and reacted at 4° C. for 24 hours. After completion of the reaction, an excess of protein was washed off, and treated with ethanolamine solution. Finally, the polymer was washed for three times with the buffer described above and with 0.1M acetate buffer (pH 4) containing 0.5M NaCl to give the phospholipase D-immobilized polymer in this order. The same reaction was conducted in the buffer (pH 8) containing no phospholipase D to prepare the control polymer.

What is claimed is:

1. In a method of decreasing cholesterol concentration in eggs or egg-containing foodstuffs by subjecting the eggs or egg-containing foodstuffs to a cholesterol-decreasing treatment, wherein the improvement comprises hydrolyzing phospholipids in the eggs or egg-containing foodstuffs at a temperature of 2° to 70° C. and for a period of time of 10 seconds to 100 hours with from $1 \times 10^{-1}$ to $1 \times 10^5$ units of phospholipase D per gram by weight of the phospholipid in the eggs or egg-containing foodstuffs while maintaining the pH of the eggs or egg-containing foodstuffs to be the pH originally possessed by the eggs or egg-containing foodstuffs, during or before the cholesterol-decreasing treatment.

2. The method according to claim 1, wherein said temperature is from 5° to 50° C., said period of time is 60 second to 50 hours and an amount of phospholipase D is from 1 to $1 \times 10^4$ units of phospholipase D per gram by weight of the phospholipid in the eggs or egg-containing foodstuffs.

3. The method according to claim 1, wherein the cholesterol-decreasing treatment is a treatment with an enzyme system which oxidizes or reduces cholesterol.

4. The method according to claim 1, wherein the cholesterol-decreasing treatment is a treatment by absorption of cholesterol using β-cyclodextrin.

* * * * *